US00PP36530P2

(12) United States Plant Patent
Gitzels

(10) Patent No.: US PP36,530 P2
(45) Date of Patent: Mar. 4, 2025

(54) ***DAHLIA* PLANT NAMED 'Baldadenast'**

(50) Latin Name: *Dahlia variabilis*
Varietal Denomination: Baldadenast

(71) Applicant: Ball Horticultural Company, West Chicago, IL (US)

(72) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 62 days.

(21) Appl. No.: 18/620,215

(22) Filed: Mar. 28, 2024

Related U.S. Application Data

(60) Provisional application No. 63/552,107, filed on Feb. 10, 2024.

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — Audrey Charles

(57) ABSTRACT

A new and distinct cultivar of *Dahlia* plant named 'Baldadenast', characterized by its double-type, dark magenta and white bicolored inflorescences, dark green-colored foliage, and vigorous, upright-mounded growth habit, is disclosed.

1 Drawing Sheet

Latin name of genus and species of plant claimed: *Dahlia variabilis*.

Variety denomination: 'Baldadenast'.

BACKGROUND OF THE INVENTION

The present invention relates to a new and distinct cultivar of *Dahlia* plant botanically known as *Dahlia variabilis* and hereinafter referred to by the cultivar name 'Baldadenast'.

The new cultivar originated in a controlled breeding program in Hem, The Netherlands during July 2017. The objective of the breeding program was the development of *Dahlia* cultivars that are freely flowering with large inflorescences, mid-season flower timing, and a vigorous, upright-mounded growth habit.

The new *Dahlia* cultivar is the result of open pollination. The female (seed) parent of the new cultivar is the proprietary *Dahlia variabilis* breeding selection coded 18446C, not patented, characterized by its double type, dark pink-colored inflorescences, medium green-colored foliage, and vigorous, upright-mounded growth habit. The male (pollen) parent of the new cultivar is unknown. The new cultivar was discovered as a single flowering plant within the progeny of the above stated open pollination during June 2018 in a controlled environment in Hem, The Netherlands.

Asexual reproduction of the new cultivar by terminal stem cuttings since June 2018 in Hem, The Netherlands and Andijk, The Netherlands has demonstrated that the new cultivar reproduces true-to-type with all the characteristics, as herein described, firmly fixed and retained through successive generations of such asexual propagation.

SUMMARY OF THE INVENTION

The following characteristics of the new cultivar have been repeatedly observed and can be used to distinguish 'Baldadenast' as a new and distinct cultivar of *Dahlia* plant:

1. Double-type, dark magenta and white bicolored inflorescences;
2. Dark green-colored foliage; and
3. Vigorous, upright-mounded growth habit.

Plants of the new cultivar differ from plants of the female parent primarily in having a darker colored inflorescence that also has a white center unlike the female parent.

Of the many commercially available *Dahlia* cultivars, the most similar in comparison to the new cultivar is Venti Pink+White Eye 'DASYVOGTYVE' U.S. Plant Pat. No. 25,798. However, in comparison, plants of the new cultivar differ from plants of 'DASYVOGTYVE' in at least the following characteristics:

1. Plants of the new cultivar have shorter and narrower ray florets than of plants of 'DASYVOGTYVE; and
2. Plants of the new cultivar have a darker ray floret color than of plants of 'DASYVOGTYVE'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldadenast'. The 19-week-old plants were grown in one-gallon containers for 14 weeks in a glass-covered greenhouse in Hem, The Netherlands. Plants were given one pinch before transplant.

DETAILED BOTANICAL DESCRIPTION

Figure 1:
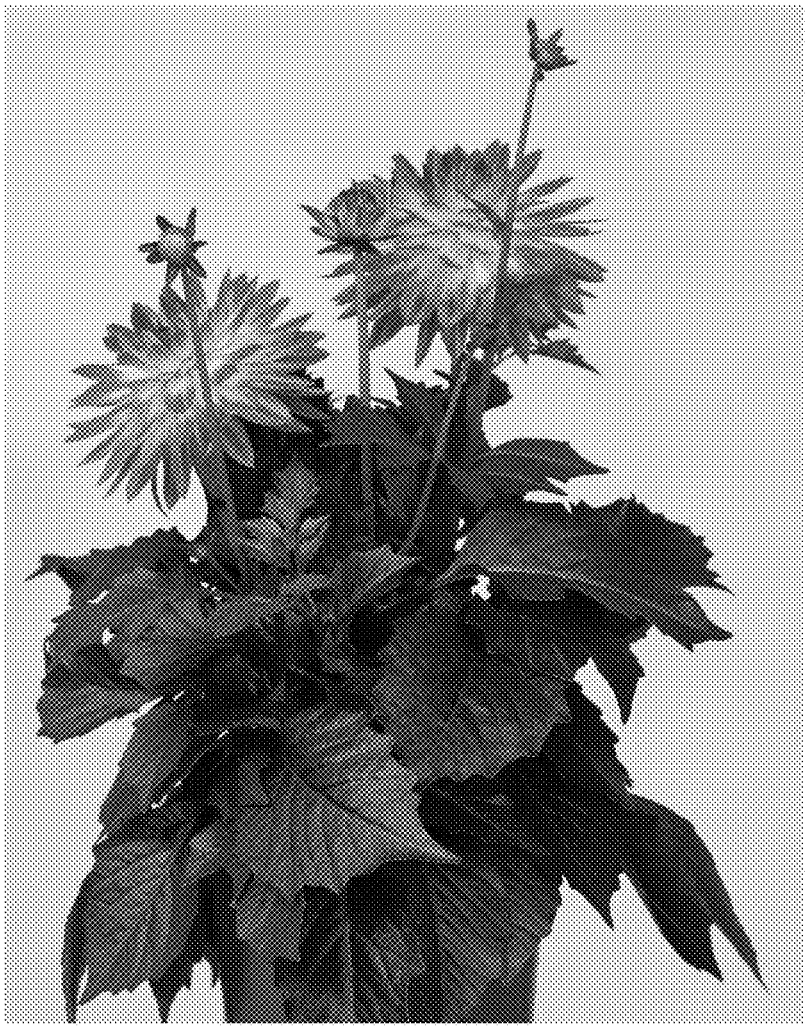
FIG. 1 illustrates a side view of the overall growth and flowering habit of 'Baldadenast'.
Figure 2:
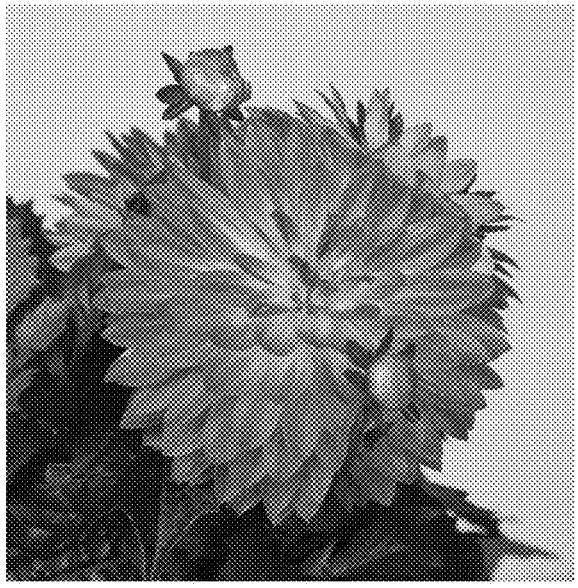
FIG. 2 illustrates a close-up view of an individual inflorescence of 'Baldadenast'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2019 edition, except where general color terms of ordinary significance are used. The color values were determined in February 2024 under natural light conditions in Boskoop, The Netherlands.

The following descriptions and measurements describe 19-week-old plants produced from cuttings from stock plants and grown in a glass-covered greenhouse under conditions comparable to those used in commercial practice. The plants were grown in Hem, The Netherlands in one-gallon containers for 14 weeks utilizing a soilless growth medium. Plants were given one pinch before transplant. Four Daminozide treatments were applied: one at 2,000 ppm ten weeks after sticking, and three 3,000 ppm treatments at 11, 13, and 15 weeks after sticking. Greenhouse temperatures were maintained at an average of approximately 61° F. (16° C.) during the day and approximately 54° F. (12° C.) during the night. Supplemental lighting was used. Measurements and numerical values represent averages of typical plants.

Botanical classification: *Dahlia variabilis* 'Baldadenast'.

Parentage:

*Female parent*.—Proprietary *Dahlia variabilis* breeding selection coded 18446C, not patented.

*Male parent*.—Unknown.

Propagation:

*Type cutting*.—Terminal stem.

*Time to initiate roots*.—Approximately 9 to 12 days.

*Time to produce a rooted cutting*.—Approximately 25 to 32 days.

*Root description*.—Fine, fibrous.

*Rooting habit*.—Freely branching.

*Tuber formation*.—Not observed.

Plant description:

*Commercial crop time*.—Approximately 7 to 9 weeks from a rooted cutting to finish in a 15 cm pot.

*Growth habit and general appearance*.—Vigorous, upright-mounded.

*Size*.—Height from soil level to top of plant plane: Approximately 28.5 cm. Height from soil level to top of foliage: Approximately 23.3 cm. Width: Approximately 35.0 cm.

*Branch*.—Quantity of lateral branches per plant: Approximately 6. Strength: Moderately strong. Length of lateral branch: Approximately 10.7 cm. Diameter of lateral branch at central internode: Approximately 7.0 mm. Length of central internode of lateral branch: Approximately 1.9 cm. Texture: Glabrous. Color: 146A, slightly tinged with 177A.

Foliage description:

*General description*.—Quantity of leaves per lateral branch: Approximately 12. Type: Simple and compound. Quantity of leaflets per compound leaf: Approximately 3 or 5. Fragrance: None detected. Arrangement: Opposite. Aspect: Petiole mostly perpendicular angle to stem with blade slightly drooping. Shape of leaf and leaflet: Ovate to broad obovate. Margin of leaf and leaflet: Widely serrate, ciliate. Apex of leaf and leaflet: Apiculate. Base of leaf and leaflet: Broadly attenuate. Venation pattern: Pinnate.

*Simple leaf*.—Length: Approximately 17.1 cm. Width: Approximately 9.0 cm. Texture of upper and lower surfaces: Sparsely pubescent with very short strigose hairs. Color of upper surface: Darker than NN137A blended with 147A. Color of lower surface: 191A blended with 194A. Length of petiole: Approximately 3.1 cm. Diameter of petiole: Approximately 4.0 mm. Texture of upper and lower surfaces of petiole: Glabrous, ciliate. Color of upper surface of petiole: 148A very slightly tinged with 177A and margined with NN137B. Color of lower surface of petiole: 146B.

*Mature compound leaf*.—Shape: Ovate in outline. Length of mature compound leaf: Approximately 16.1 cm. Width of mature compound leaf: Approximately 15.4 cm. Length of terminal leaflet: Approximately 13.5 cm. Width of terminal leaflet: Approximately 7.5 cm. Length of lateral leaflet: Approximately 8.1 cm. Width of lateral leaflet: Approximately 4.3 cm. Texture of upper and lower surfaces: Sparsely pubescent with very short strigose hairs. Color of upper surface: Darker than NN137A blended with 147A, tinted with N186C at rachis attachment. Color of lower surface: 191A blended with 191B. Length of petiole of mature compound leaf: Approximately 3.7 cm. Length of rachis: Approximately 2.9 cm. Diameter of petiole and rachis of mature compound leaf: Approximately 4.0 mm. Texture of upper and lower surfaces of petiole and rachis: Glabrous, ciliate. Color of upper surface of petiole and rachis: 148A very slightly tinged with 177A and margined with NN137B. Color of lower surface of petiole and rachis: 146B.

Flowering description:

*Flowering habit*.—'Baldadenast' is freely flowering under outdoor growing conditions with substantially continuous blooming from summer through autumn.

*Lastingness of individual inflorescence on the plant*.—Approximately 2 weeks.

Inflorescence description:

*General description*.—Type: Double, composite, consisting of multiple rows or ray florets, and disc florets, persistent. Aspect: Facing upward and slightly outward. Arrangement: Terminal, arising from leaf axils on strong peduncles positioned over the foliage. Disc and ray florets arranged acropetally on a capitulum. Quantity per plant: Approximately 3. Fragrance: None detected. Shape: Hemispherical to near spherical when ray florets are fully open. Inflorescence diameter: Approximately 12.6 cm. Inflorescence depth: Approximately 9.4 cm. Disc diameter: Approximately 1.4 cm. Receptacle diameter at base: Approximately 1.1 cm. Receptacle depth: Approximately 2.0 mm. Receptacle color: 143A blended with 144A.

*Peduncle*.—Strength: Strong. Aspect: Erect. Length: Approximately 16.9 cm. Diameter: Approximately 4.0 mm. Texture: Glabrous, slightly glaucous. Color: 146A blended with 148A, and slightly to moderately tinged with 177A.

*Bud*.—Rate of bud opening: Generally takes 2 weeks for bud to progress from first color to fully open flower. Quantity per plant: Approximately 7.

*Bud just before opening*.—Shape: Oblate. Depth at first color: Approximately 1.1 cm. Diameter at first color:

Approximately 1.7 cm. Texture: Glabrous. Color: Outer surface of the phyllaries N144A with base of 143A to 143B and bud upper center slightly tinged with 56A.

*Ray florets*.—Quantity per inflorescence: Approximately 250. Arrangement: Imbricate, in multiple whorls. Aspect: Flat to very slightly concave. Shape: Oblanceolate. Margin: Entire. Apex: Apiculate. Base: Attenuate. Appearance: Matte, slightly velvety. Length: Outer most approximately 5.7 cm and innermost approximately 3.0 cm. Width: Outer most approximately 1.6 cm and innermost approximately 1.0 cm. Texture of upper surface: Glabrous. Texture of lower surface: Glabrous, ribbed. Color of upper surface when first and fully open: 60B with approximately lower half a blend of 4D with 155D and base of 2C. Color of lower surface when first and fully open: 59D with approximately lower half a blend of 4D with 155D. Color of upper surface before senescence: 58B transitioning towards the margins to N57C and approximately lower one-third of 155C with base of 1C to 1D. Color of lower surface before senescence: 55B with N57C to N57D and approximately lower one-third of N155C.

*Disc florets*.—Quantity per inflorescence: Approximately 30. Arrangement: Massed in center of inflorescence. Aspect: Erect. Shape: Tubular. Margin: Entire. Apex: 5 acute tips. Base: Fused. Length: Approximately 1.2 cm. Diameter at apex: Approximately 3.0 mm. Diameter at base: Approximately 1.2 mm. Texture: Glabrous. Color when fully open: 13A with midsection of 1A and base of 145A to 145B.

*Outer phyllaries*.—Quantity: Approximately 6 to 8. Aspect: Strongly reflexed. Shape: Ovate to elliptic. Margin: Entire. Apex: Acute. Base: Truncate. Length: Approximately 1.9 cm. Width: Approximately 6.0 mm. Texture of upper and lower surfaces: Glabrous. Color of upper surface: NN137B. Color of lower surface: 137B with venation of NN137A.

*Inner phyllaries*.—Quantity: Approximately 1 per floret. Shape: Lanceolate, imbricate. Margin: Entire. Apex: Broadly acute to obtuse. Base: Truncate. Length of outermost: Approximately 2.3 cm. Width of outermost: Approximately 1.0 cm. Length of innermost: Approximately 1.4 cm. Width of innermost: Approximately 6.0 mm. Texture of upper and lower surfaces: Glabrous. Color of upper and lower surfaces: Blend of N144B with 150B, translucent with 143A at base of outermost.

*Reproductive organs*.—Androecium: On disc florets. Stamen quantity: 5 per floret. Stamen length: Approximately 8.0 mm. Anther shape: Linear. Anther length: Approximately 4.0 mm. Anther color: 1A. Pollen amount: Moderate. Pollen color: 17A. Gynoecium: On disc florets. Pistil length: Approximately 9.0 mm. Stigma shape: 2 branched. Stigma length: Approximately 3.0 mm. Stigma width: Approximately 4.0 mm. Stigma color: 17B. Style length: Approximately 6.0 mm. Style color: 145D. Ovary length: Approximately 1.0 mm. Ovary color: 145A to 145B.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldadenast', substantially as herein illustrated and described.

* * * * *